United States Patent
Dörre et al.

(10) Patent No.: US 8,860,677 B2
(45) Date of Patent: Oct. 14, 2014

(54) OPERATING UNIT, MEDICAL DEVICE AND METHOD FOR OPERATING SAID UNIT

(75) Inventors: Helmut Dörre, Nürnberg (DE);
Dominik Hartleib, Nürnberg (DE);
Harald Karl, Fürth (DE); Heiko Oester, Forchheim (DE); Stefan Sattler, Forchheim (DE); Matthias Wolfgang, Forchheim (DE)

(73) Assignee: Siemens Aktiengesellschaft, Munich (DE)

( * ) Notice: Subject to any disclaimer, the term of this patent is extended or adjusted under 35 U.S.C. 154(b) by 319 days.

(21) Appl. No.: 13/389,877

(22) PCT Filed: Aug. 10, 2010

(86) PCT No.: PCT/EP2010/061573
§ 371 (c)(1),
(2), (4) Date: Apr. 9, 2012

(87) PCT Pub. No.: WO2011/018442
PCT Pub. Date: Feb. 17, 2011

(65) Prior Publication Data
US 2012/0188187 A1 Jul. 26, 2012

(30) Foreign Application Priority Data
Aug. 11, 2009 (DE) .......... 10 2009 036 941

(51) Int. Cl.
*G06F 3/041* (2006.01)
*G06F 3/01* (2006.01)

(52) U.S. Cl.
CPC .............. *G06F 3/041* (2013.01); *G06F 3/016* (2013.01)
USPC ................... 345/173; 345/156; 340/407.1

(58) Field of Classification Search
CPC ....... G06F 3/041; G06F 3/0414; G06F 3/042; G06F 3/043; G06F 3/044; G06F 3/045; G06F 2203/04106; G09G 2308/08; G09G 23/28
USPC ................ 345/156, 173–178; 434/262, 272; 178/18.04–18.07, 18.09; 340/407.1
See application file for complete search history.

(56) References Cited

U.S. PATENT DOCUMENTS

| | | | |
|---|---|---|---|
| 6,504,530 B1 | 1/2003 | Borgnis | |
| 7,479,947 B2* | 1/2009 | Pihlaja | 345/173 |
| 8,385,885 B2* | 2/2013 | Hainzl | 455/411 |
| 8,483,802 B2* | 7/2013 | Kalpin et al. | 600/424 |
| 2007/0080951 A1* | 4/2007 | Maruyama et al. | 345/173 |
| 2008/0004633 A1* | 1/2008 | Arata et al. | 606/130 |

(Continued)

FOREIGN PATENT DOCUMENTS

| | | |
|---|---|---|
| CN | 1496549 A | 5/2004 |
| DE | 101 51 236 A1 | 5/2003 |
| EP | 2 009 542 A1 | 12/2006 |
| EP | 2 073 107 A1 | 6/2009 |

*Primary Examiner* — Joe H Cheng

(57) ABSTRACT

An operating unit for a medical device is proposed. The operating unit has at least one display, at least one transparent, touch-sensitive first input field, and at least one transparent, touch-sensitive second input field. The at least one second input field is disposed between the at least one display and the at least one first input field. At least one device provides a haptically perceivable feedback after successful operation of the operating unit.

15 Claims, 6 Drawing Sheets

(56) References Cited

U.S. PATENT DOCUMENTS

| | | |
|---|---|---|
| 2008/0084384 A1 | 4/2008 | Cruz-Hernandez |
| 2008/0259046 A1* | 10/2008 | Carsanaro ..................... 345/173 |
| 2009/0002329 A1 | 1/2009 | Van Genechten et al. |
| 2009/0176534 A1 | 7/2009 | Lee et al. |
| 2009/0234302 A1* | 9/2009 | Hoendervoogt et al. 604/288.01 |
| 2010/0156818 A1* | 6/2010 | Burrough et al. ............. 345/173 |
| 2012/0103776 A1* | 5/2012 | Walker et al. ................. 200/5 A |
| 2013/0150708 A1* | 6/2013 | Van Vorhis ................... 600/424 |

* cited by examiner

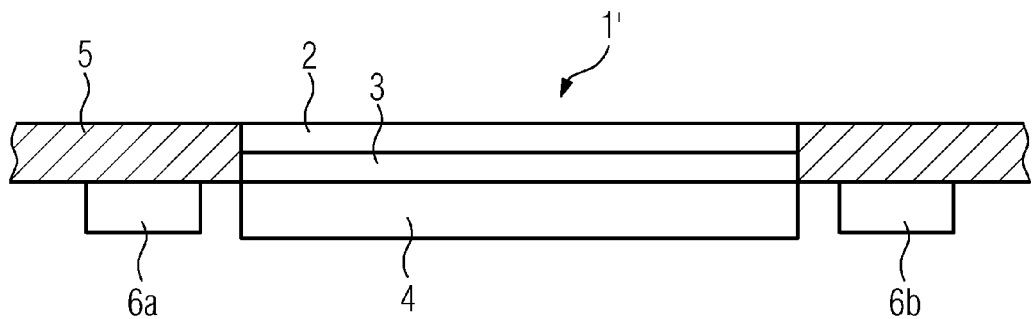
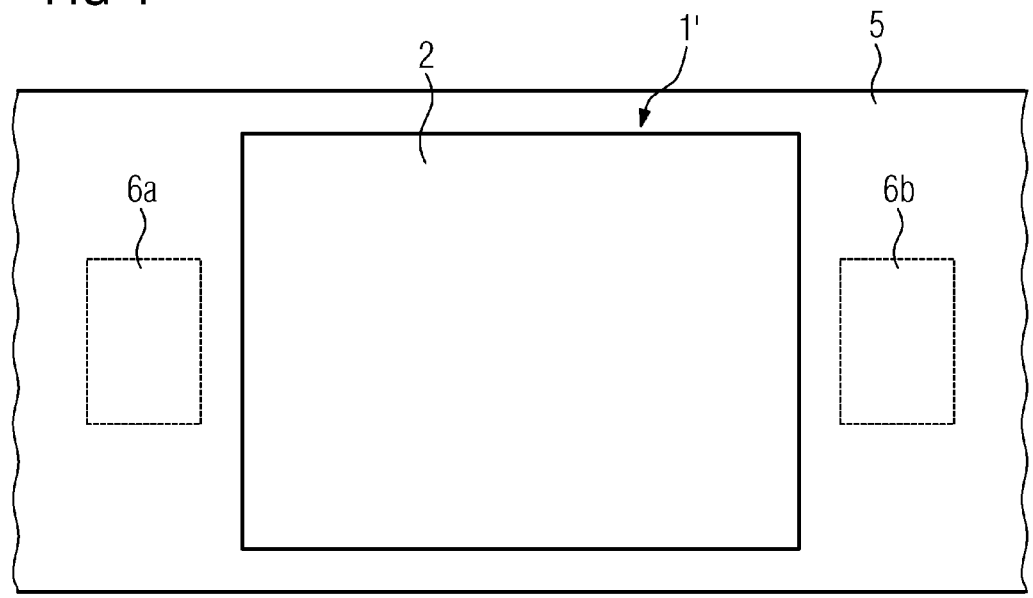

US 8,860,677 B2

OPERATING UNIT, MEDICAL DEVICE AND METHOD FOR OPERATING SAID UNIT

CROSS REFERENCE TO RELATED APPLICATIONS

This application is the US National Stage of International Application No. PCT/EP2010/061573, filed Aug. 10, 2010 and claims the benefit thereof. The International Application claims the benefits of German application No. 10 2009 036 941.4 filed Aug. 11, 2009, both of the applications are incorporated by reference herein in their entirety.

FIELD OF THE INVENTION

The invention relates to an operating unit comprising at least one display, at least one transparent, touch-sensitive first input field and at least one transparent, touch-sensitive second input field. The invention further relates to a medical device with such an operating unit as well is to a method for performing a safety-relevant action by means of such a medical device.

BACKGROUND OF THE INVENTION

In the operation of medical devices, especially of diagnostic and intervention systems in angiography, cardiology or neurology, the very widest range of operating units are used for control of components of the respective medical device. A safety-relevant action of the devices is to be seen here for example as an action such as one in which a patient or the operating personnel of the device can come to harm indirectly or directly.

A movable component of a medical device to be controlled is for example the C-arm which serves as a carrier for imaging components, for X-ray devices for example. Specifically in the operation of medical devices in which such a movable component has to be positioned in respect of a person, it is important that a hardware error does not lead to incorrect behavior of the movable components. In the worst case the patient can be seriously injured by an inadvertent, uncontrolled or automatic movement of such a movable component.

But even operation of components and functional units which do not directly result in adverse effects on the patient from movements of components should if possible be able to be executed so that errors are avoided. Such a functional unit would for example be a detector system or a radiation collimator, wherein an inadvertent repositioning of imaging components could prevent use of image data obtained. The examination would therefore have to be repeated and the patient subjected to renewed irradiation for example. A further functional unit would be provided for example by an on switch for x-radiation, wherein incorrect operation can likewise cause injury to a patient.

Furthermore it is helpful for the operator of a medical device to obtain haptic feedback through the operating unit, even through sterile coverings or gloves, about a successful device operation performed. Since the primary attention of the operator of a medical device for diagnosis and/or intervention is devoted as a rule to a patient or to the examination results obtained, the necessity to visually check the operating unit is disruptive and is designed to be largely avoided through the haptic feedback.

Previously the interfaces between medical devices, especially of diagnosis and intervention systems in angiography, cardiology and neurology and the operators, were implemented by means of sensors, which usually possess two mechanically-coupled contacts which can both be interrogated. This reveals a failure of one of the contacts if necessary, makes possible the diagnostic establishment of an error and prevents an inadvertent and unchecked action of the medical device.

Sensors in combination with a liquid crystal display are already known from DE 101 51 236 A1 for medical devices, which as well as allowing operation, simultaneously make it possible to display information.

In recent years touch-sensitive input fields have been developed which are also known by the names touchscreen touchpad, sensor screen and the like. These involve an operating unit for a processing unit in which, by touching selected areas of the screen, a program sequence on the processing unit can be influenced. The image in this case can be generated either dynamically by means of displays, monitors or via a projection or alternatively also by a static, for example printed, image. Such an input field can have a single or a plurality of touch-sensitive areas able to be actuated independently of one another.

A touchscreen is known from U.S. Pat. No. 6,504,530, which has a number of touch-sensitive input fields. These can for example be used in combination with a liquid crystal display or a cathode-ray tube to generate image information to be selected by touch. In this case a touch, which is detected by means of a first touch-sensitive input field, can be confirmed by a second touch-sensitive input field, which preferably is of another type or operates in a different way. Incorrect operation or unintentional operation is largely prevented by this.

For operation of safety-relevant device functions of medical devices which can have negative effects on a patient and/or on the operating personnel, touch-sensitive input fields have not previously been used, since these do not fulfill the requirements for fault tolerance and/or sufficient haptic feedback.

SUMMARY OF THE INVENTION

The object of the invention is thus to provide an improved operating unit, especially for medical devices, comprising at least one touch-sensitive input field.

The object is achieved by an operating unit comprising at least one display, at least one transparent, touch-sensitive first input field and at least one transparent, touch-sensitive second input field, wherein the least one second input field is disposed between the least one display in the at least one first input field, as well as at least one device which provides a haptically perceivable feedback after successful operation of the operating unit.

The at least one display is visible through the at least one first input field and the at least one second input field. The display involved is preferably a liquid crystal display, especially an active matrix display, an OLED display or similar.

The actuation of the at least one first input field and of the at least one second input field can be interrogated simultaneously in order to carry out a plausibility check on the operating action undertaken. If the operating unit is actuated successfully, wherein the at least one first operating field and the at least one second operating field have been actuated simultaneously, the operator is provided by the device with a unique haptic feedback about the success of the operating action.

The touch-sensitive input fields form redundant systems in this case, which make it possible to check the operability of the other system in each case. The simultaneous presence of a touch the at least one first input field and the actuation of a second input field lying behind it means that there is a high probability that the operator has performed an intentional operating action, which can consequently be implemented. A defect in the area of an input field is uniquely identifiable from the fact that in this case a simultaneous operating action of both systems is not present.

The inventive operating unit can be used very flexibly since there can be almost any arrangement on a device. The operating unit makes barely any demands on the place of use, the mounting location, the available lighting conditions, etc.

As a result of a possible change of the screen of the display, complicated and freely-configurable device controls can also be executed with just a single operating unit or just a small number of operating units.

In addition the display can be used, at times when an actuation of the operating unit is not necessary or required, to display data and/or information and/or pictures which are helpful to the operator. Thus for example, after a device, especially an examination device, has been started, an online display of examination results or the like can be shown on the display.

In general one of the already known operating fields, the functioning of which is sufficiently well known and does not require further explanation here, can be used as the transparent, touch-sensitive first and/or second input field. However is has proved useful to use a resistance-controlled input field, capacitance-controlled input field, sound wave-controlled input field or optical input field as the first and/or second input field.

It is preferred in such cases for the at least one first input field and the at least one second input field to involve different types of input field. In any event the first and second input field are to be selected so that these fields do not influence each other. Thus in a preferred embodiment a capacitive input field can be selected for a first input field and a resistive input field for a second input field. In this case is preferably based on Atmel's digital charge-transfer technology or on Cypress's "CapSense/True Touch" technology. These capacitive input fields only need a passive film, for example made of glass or transparent plastic, with electrodes as sensors which consist of transparent electrically-conductive Indium-Tin Oxide (ITO). However other transparent, electrically-conductive materials are also able to be used as electrodes.

While a resistive second input field preferably detects the exact coordinates of the operator's touch, the same resolution is not an absolute requirement for the capacitive first input field. This can likewise deliver coordinates to specify the touch position but can also simply consist of individual surfaces which embody capacitive keys. Such a combination of a capacitive first input field and a resistive second input field ensures that any possibility of the fields influencing one another is excluded.

Preferably the at least one first input field is arranged on the at least one second input field to cover the same area. However this does not exclude a number of transparent films, adhesive films, glass films or the like and to other transparent combinations thereof being able to be located between a first input field and a second input field.

In a preferred embodiment the at least one first input field and the at least one second input field are arranged on the display to cover the same area as the latter. However this does not exclude a number of transparent films, adhesive films, glass films or the like, as well as transparent combinations thereof being able to be located between a second input field and the display.

It has proved worthwhile for the display to have a front side facing towards an operator and for the at least one first input field and the at least one second input field to at least partly cover this front side. Especially preferably the at least one first input field covers the front side of the display completely.

The at least one device which provides a haptically perceivable feedback after the operating unit has been successfully operated, is preferably connected to a rear side of the at least one display facing away from the user and/or to a carrier of the display. The device should generate a vibration, pulsing or shaking of at least an area of the operating unit at which the operation was just carried out perceivable to an operator of the operating unit. In this case the haptic feedback is in particular embodied so strongly that a user notices it despite wearing gloves or other protective coverings. In particular the at least one device which provides a haptically perceivable feedback after the operating unit has been operated is formed by a vibration motor.

Preferably warning or status indicators which are generated by different haptically perceivable signals output by the device are also transmitted to a user via the haptic feedback. Thus for example through an operating unit by means of which an operator for example controls a positioning of a component, reaching and end stop for a movement of the component, an action currently being performed or the threat of a collision between the component and another component if the selected movement is continued can be indicated by output of a respective modified haptically perceivable signal. To this end the device can be configured for example to generate different haptically perceivable vibration patterns which are assigned to specific states of the device to be operated and which inform the operator or generate an alarm without the latter having to visually read off corresponding information from the display or other device indicators.

It has proven worthwhile for a display, a first input field and a second input field respectively to be connected to each other. This guarantees an especially low profile of the operating unit with the consequent small space requirement.

The at least one first input field can be located directly on the side of the operating unit facing towards the user. This can however equally well be covered by a transparent protective film. This protective film should however not adversely affect the functioning of the at least one first input field and of the at least one second input field.

A person skilled in the art is readily able to establish electrical contact between a display, a first and second input field and also a device which handles haptic feedback.

A medical device which is equipped with a least one inventive operating unit has proven especially useful. The medical device can for example be a magnetic resonance tomograph, a conventional X-ray device, specifically also an interventional or cardiological angiography system, a computer tomograph or a radiation therapy device.

The inventive operating unit is however also suitable for other machines or systems in which increased safety requirements apply, such as building machines, robots and the like.

In particular a medical device with at least one component is involved, which is able to be positioned by means of a positioning device, wherein by means of the at least one operating unit an input of a required position of the at least one component and a corresponding activation of the positioning device for adjusting the required position is able to be effected. A movement of the component can be put in train by briefly touching the operating unit but also carried out during the continued touching action.

But other components of a medical device which are not movable and the activity of which is still safety-relevant despite this are preferably operated by means of at least one inventive operating unit.

The medical device preferably comprises at least one processing unit which is configured to receive at least one first signal able to be generated when the at least one first input field is touched and to receive at least one second signal able to be generated when the at least one second input field, which is located in the direction of touch behind the at least one first input field, is touched simultaneously, to process said signal and only in the event that the at least one first signal and the at least one second signal are present at the same time, to output at least one control signal for activating the at least one device and executing a safety-relevant action, especially for activating a positioning device.

The operating unit can be activated in this case not only by direct "touching" of the at least one first input field which faces towards the operator. Touching a surface of the operating unit in which the at least one first operating field is not touched directly but is however activated by the touch also comes into consideration.

In accordance with the invention a method is performed for carrying out a safety-relevant action by means of a medical device comprising an inventive operating unit, especially for positioning at least one component of a medical device, wherein only in the event of the at least one first input field being touched and at the same time the at least one second input field located in the direction of touch behind the at least one first input field being actuated, the at least one device is activated accordingly and a safety-relevant action is executed.

This prevents an inadvertent operation of the medical device or a defect at an operating unit leading to an action which could indirectly or directly cause halm to a patient and/or to the operating personnel.

It is especially preferred in the method for
a) the at least one first input field to be touched and through this the least one first signal to be generated;
b) optionally simultaneously the at least one second input field located in the direction of touch behind the at least one first input field to be actuated and by this if necessary at least one second signal to be generated;
c) the at least one first signal and if necessary the at least one second signal to be transferred to the at least one processing unit;
d) only if the at least one first signal and the at least one second signal are present at the same time, for the at least one device to be activated, a control signal for executing the safety-relevant action to be generated and for this action to be executed.

In particular a control signal is transferred to a positioning device and as a result at least one component is positioned by means of the positioning device in accordance with the control signal.

Preferably a duration of the actuation of the at least one operating unit is detected and only if a minimum duration is exceeded are the first and/or the second signal accepted by the processing unit. The duration of the actuation in this case can for example be determined by the processing unit and compared with a predetermined minimum duration, which as a rule corresponds to the usual duration of a desired actuation of the operating unit. The operating safety is greatly enhanced by the detection and evaluation of the duration of the actuation, since a short, inadvertent touching of the operating unit does not immediately lead to an actuation of the operating unit.

Furthermore a maximum allowable operating duration can be monitored, provided this is possible and/or necessary within the framework of the application.

The signal for activating the device which provides the operator with haptic feedback of a successful operation of the operating unit, especially contains information about the type of haptic feedback to be output, for example in respect of a required vibration strength and/or the required vibration pattern.

BRIEF DESCRIPTION OF THE DRAWINGS

FIGS. 1 to 10 are intended to illustrate possible exemplary embodiments of operating units and their use. The figures show:

FIG. 1 a first operating unit viewed from the side;
FIG. 2 the first operating unit in accordance with FIG. 1 viewed from above;
FIG. 3 a second operating unit viewed from the side;
FIG. 4 the second operating unit in accordance with FIG. 3 viewed from above;
FIG. 5 a third operating unit viewed from the side;
FIG. 6 a fourth operating unit viewed from the side;
FIG. 7 a fifth operating unit viewed from the side;
FIG. 8 the fifth operating unit in accordance with FIG. 7 viewed from above;
FIG. 9 a schematic diagram of an electric circuit of an operating unit in accordance with FIG. 2 in a device; and
FIG. 10 a flowchart of an exemplary embodiment.

DETAILED DESCRIPTION OF THE INVENTION

Figure 1:
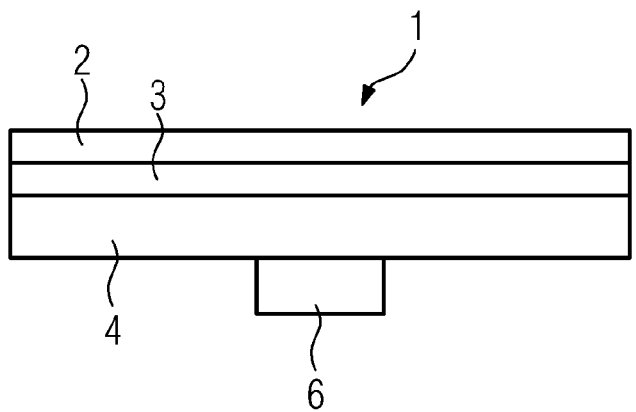
Figure 2:
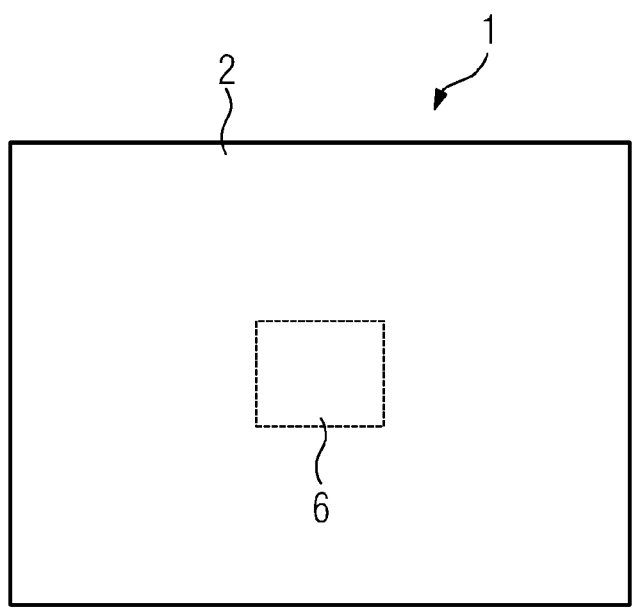

FIG. 1 shows a schematic of a first operating unit 1 viewed from the side. FIG. 2 shows a schematic of the first operating unit 1 in accordance with FIG. 1 viewed from above.

The operating unit 1 comprises a display 4 in the form of a liquid-crystal display, also known as an LCD, a transparent, touch-sensitive first input field 2 and a transparent, touch-sensitive second input field 3.

On the front side of the display 4 facing towards the operator displayed image information can be read out visually by the operator through the transparent first input field 2 and the transparent second input field 3. In this example the display 4 and the first and second input field 2, 3 are the same size and disposed to cover the same area as each other. The display 4 and the two input fields 2, 3 can however alternatively cover different areas and thus be disposed only partly overlapping.

Located on the rear side of the display 4 facing away from the operator of the operating unit 1 is a device 6, which, after the operating unit 1 has been successfully operated by an operator, provides an operator with haptically perceivable feedback that the operation was successful. The device 6 typically involves a vibration motor which is in a position, if necessary in collaboration with a carrier unit, such as a baseplate or a housing, into which the operating unit 1 is built, to impart a haptically perceivable vibration to the operating unit 1. The type and/or duration of the vibration in this case is characteristic of the type of action performed and/or a state of the device operated with the operating unit 1.

The electrical contact between the display 4 and the touch-sensitive input fields 2, 3 is not shown in detail here for reasons of clarity and is sufficiently well known to the person skilled in the art. The information shown on the display 4 is usually fed in via a processing unit.

The touch-sensitive first input field 2 can involve any known type of input field, for example a resistive, capacitive, sound-wave or optically-controlled input field. Here the first input field 2 is preferably a capacitive input field.

The touch-sensitive second input field 3 can in principle likewise involve any known type of input field, for example a resistive, capacitive, sound-wave or optically-controlled input field. However the second input field 3 is preferably of a different type from the first input field 2, in order where possible to avoid any mutual influence between them. Here the second input field 2 is preferably a resistive input field.

FIG. 3 shows a schematic of a second operating unit 1' viewed from the side. FIG. 4 shows the second operating unit 1' in accordance with FIG. 3 viewed from above.

The operating unit 1' again comprises a display 4, a transparent, touch-sensitive first input field 2 and a transparent, touch-sensitive second input field 3. On the front side of the display 4 facing towards a user, displayed image information can be read out visually by the operator through the transparent first input field 2 and the transparent second input field 3. In this exemplary embodiment the display 4 and the first and second input field 2, 3 are the same size and disposed to cover the same area as each other. The display 4 and the two input fields 2, 3 can however alternatively cover different areas and thus merely be disposed partly overlapping.

The operating unit 1' further comprises in accordance with FIG. 3 a carrier unit 5 or a base plate, which is shown here in cross-section and serves as a mechanical carrier for the display 4, the first input field 2 and the second input field 3.

Located on the rear side of the carrier unit 5 facing away from the operating unit 1' are devices 6a, 6b which, after the operating unit 1' has been successfully operated by an operator, provide an operator with haptically perceivable feedback that the operation was successful. The devices 6a, 6b involve vibration motors for example, which are in a position to impart haptically perceivable vibration to the operating unit 1. The embodiment of the carrier unit 5 is able to be varied in such cases within wide limits and it does not have to be a component of the operating unit 1'.

Figure 5:
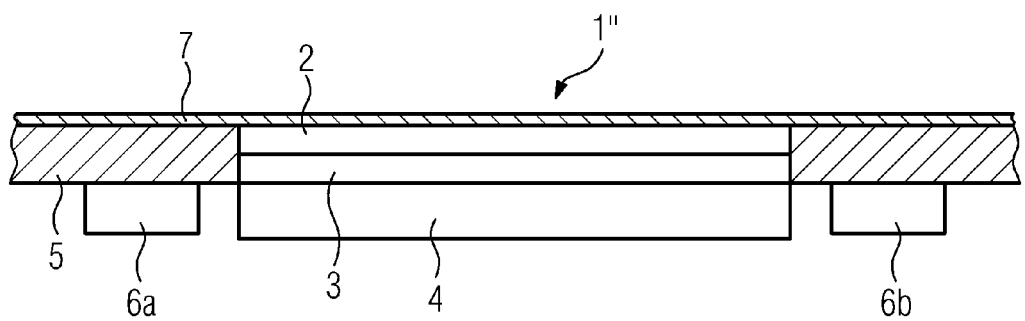

FIG. 5 shows a schematic of a third operating unit 1" viewed from the side. The third operating unit 1" is constructed in a similar manner to the unit shown in FIG. 3, with the same reference characters identifying the same elements. Disposed on the side of the third operating unit 1" facing towards an operator is a transparent protective film 7 for protection against mechanical and/or corrosive stresses, which can be a component of the third operating unit 1", but does not have to be. The image information displayed by the display 4 can be read out visually by the operator through transparent input fields 2, 3 and the protective film 7. The protective film 7 may not adversely affect the operability of the input fields 2, 3 when touched in such cases.

Figure 6:
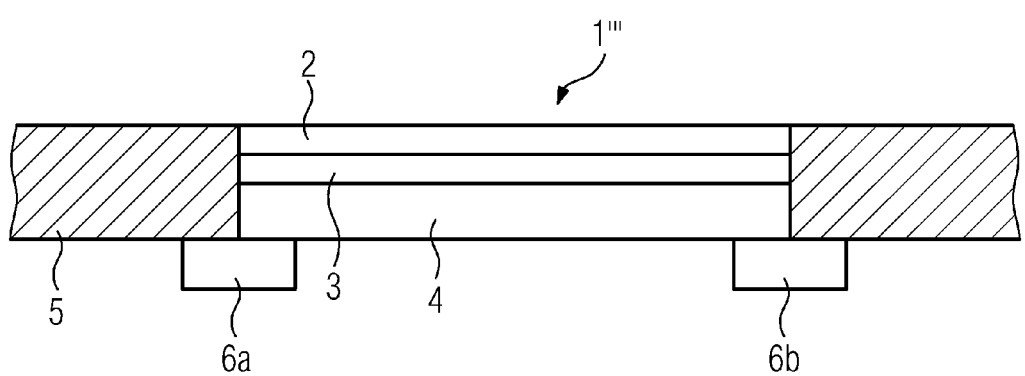

FIG. 6 shows a schematic of a fourth operating unit 1' viewed from the side. The fourth operating unit 1'''' is similar in its construction to the unit shown in FIG. 3, with the same reference characters identifying the same elements. The fourth operating unit 1' comprises a carrier 5, which is shown in cross-section and serves as a carrier for the display 4, the first input field 2 and the second input field 3. Located on a rear side of the carrier unit 5 facing towards an operator of the fourth operating unit 1''', overlapping with display 4, are devices 6a, 6b, after the operating unit 1''' has been successfully operated by an operator, provide an operator with haptically perceivable feedback. The devices 6a, 6b typically involve vibration motors, which are in a position to impart haptically perceivable vibration to the fourth operating unit 1''' inclusive or exclusive of the carrier unit 5. The embodiment of the carrier unit 5 is able to be varied in such cases within wide limits and it does not have to be a component of the operating unit 1'''.

Figure 7:
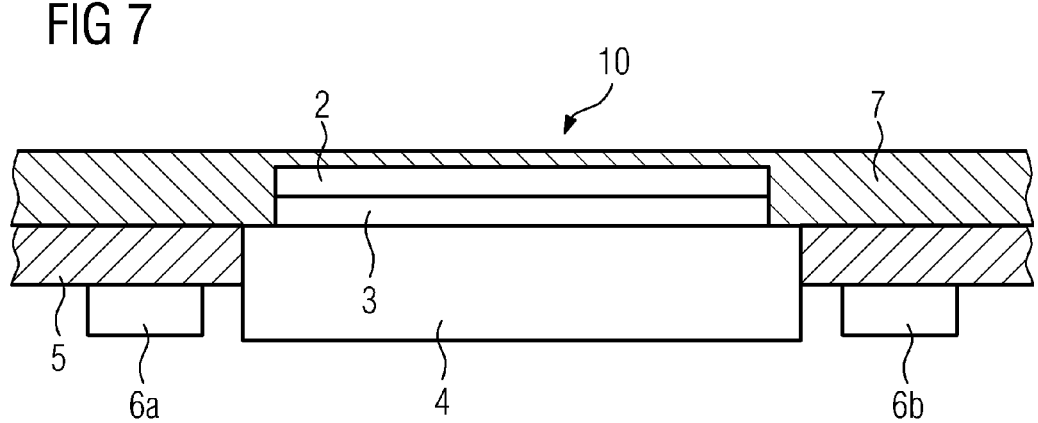

FIG. 7 shows a schematic of a fifth operating unit 10 viewed from the side. The fifth operating unit 10 is similar in its construction to the third operating unit 1" shown in FIG. 5, with the same reference characters identifying the same elements. By contrast with said unit, the fifth operating unit 10 here has a first input field 2 and a second input field 3 which are disposed to cover the same area as each other, but only partly cover the display 4.

Figure 8:
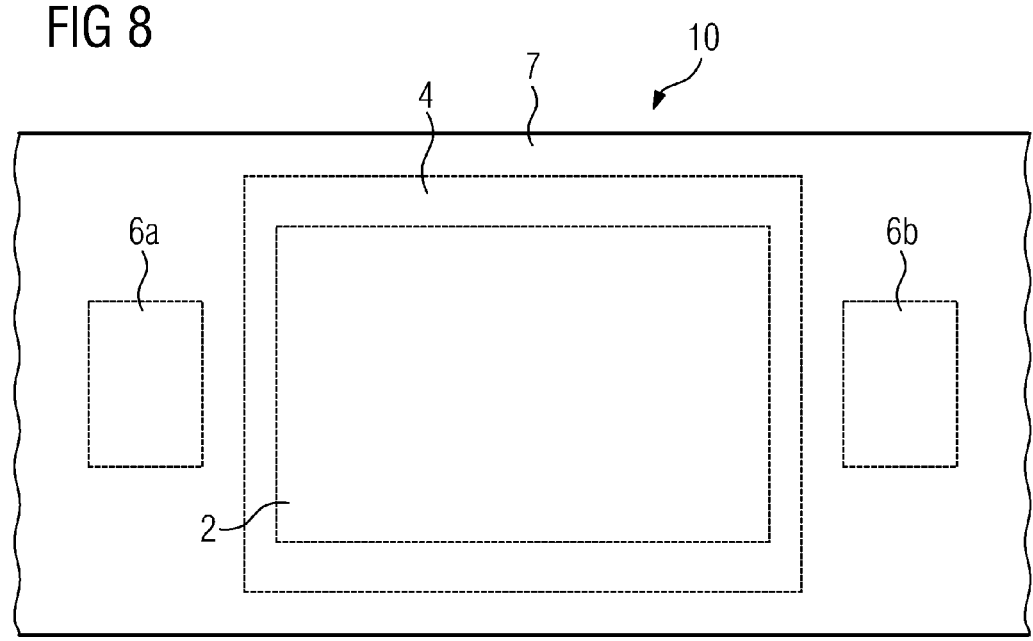

FIG. 8 shows the fifth operating unit 10 in accordance with FIG. 7 viewed from above, wherein the transparent protective film 7 has been broken through in one area to shown the elements below it.

If an operator actuates the operating unit 1, 1', 1", 1''', 10, intentionally, he simultaneously actuates the first input field 2 and the second input field 3. This generates a first switching signal S1 by means of the first input field 2 and simultaneously a second switching signal S2 by means of the second input field 3.

Figure 9:
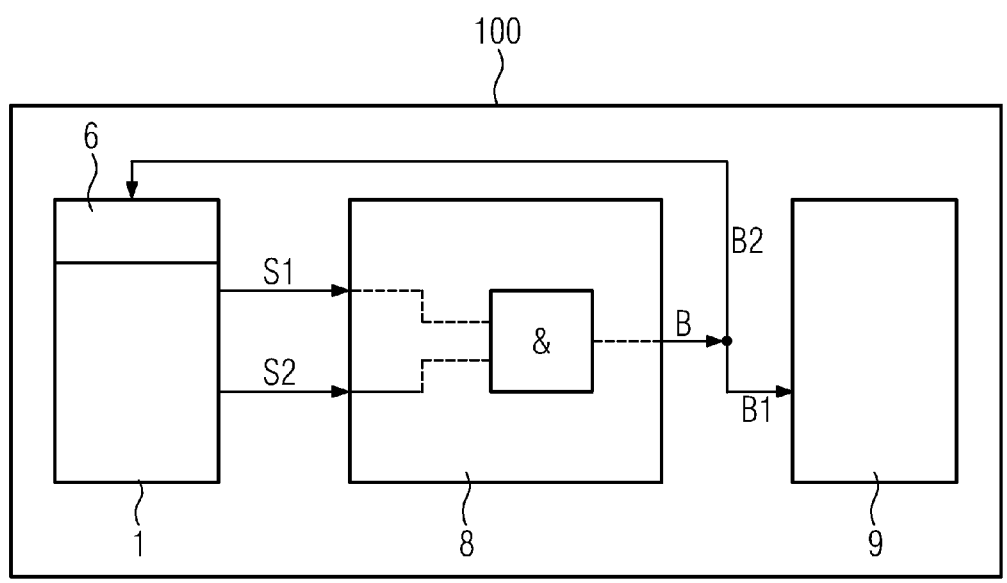
Figure 10:
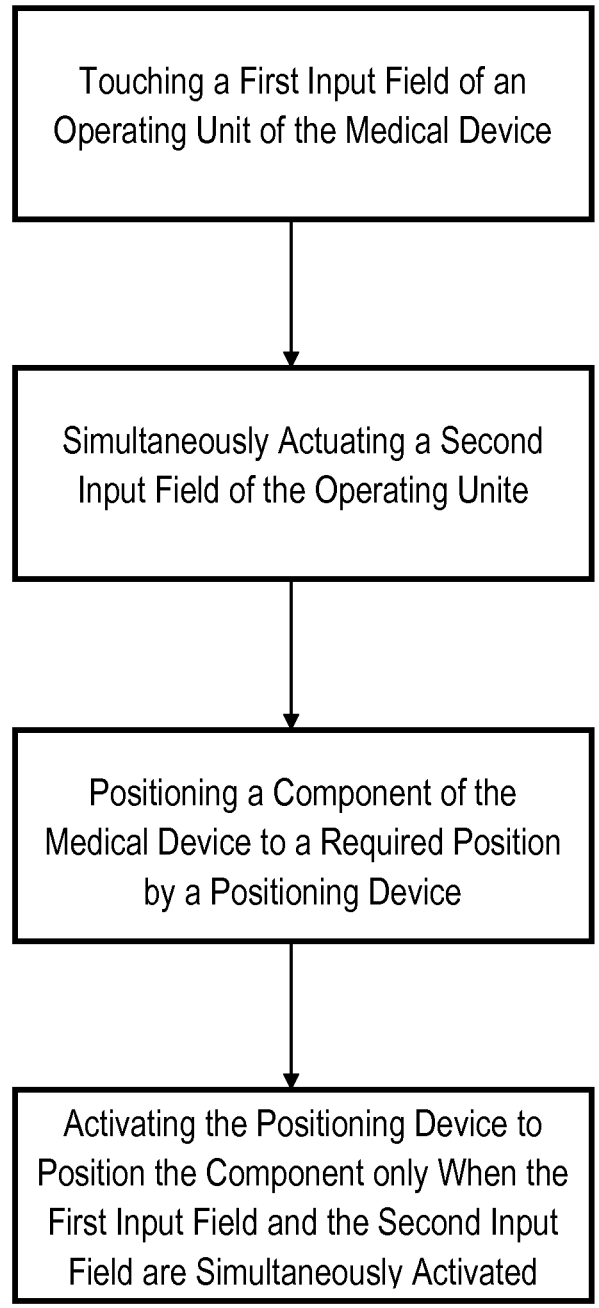

FIG. 9 shows a schematic of an electric circuit of the first operating unit 1 in accordance with FIGS. 1 and 2, which is built into a medical device 100 or another sort of device. The first switching signal S1, which is generated when the first input field 2 is touched or actuated, is transferred to a processing unit 8. The processing unit 8 here is a component of the medical device 100, but does not always have to be. The second switching signal S2, which is generated on actuation of the second input field 3, is likewise transferred to the processing unit 8. The processing unit 8 is configured to perform a synchronization as to whether both switching signals S1 and S2 are present at the same time. The processing unit 8 can also be configured, to determine the duration of the actuation of the first input field 2 and the second input field 2, 3 and only when the duration exceeds a defined minimum duration, to classify them as plausible and accept them. Only when both switching signals S1 and S2 are present at the same time, especially for more than a minimum duration and/or not longer than a maximum duration, at least one control command or control signal B is output by the processing unit 8. In this case at least one first control command B1 is transferred to the device 6, so that said device is activated and generates haptic feedback to the operator that the operator action was successful. Furthermore at least one second control command B2 is output to carry out a safety-relevant action, for example to activate a positioning apparatus 9 of the medical device 100, in order for example to change the position of a C-arm of the medical device 100.

If only one of the switching signals S1 or S2 is present and/or if a signal is not present for the required minimum duration or is present for too long, no control command is generated by the processing unit 8. If necessary an error message is output, which makes the operator aware that the operating unit 1 has not been operated correctly, for example that only the first input field 2 was actuated, but the second input field 3 was not actuated however, or that a defect is present. Such a defect can be present in an outage of the first input field 2 or the second input field 3.

The redundant detection of the switching signals S1 and S2 is of importance especially for devices in which incorrect operation or a defect of the operating unit can give rise to serious consequences.

The exemplary embodiments shown in FIGS. 1 to 9 merely serve to illustrate the invention. Thus an operating element can include a plurality of first and second input fields each comprising one or more touch-sensitive areas, include input fields in more than two different embodiments, etc., without departing from the inventive idea.

The invention claimed is:
1. An operating unit, comprising:
   a display;
   a first transparent and touch-sensitive input field;
   a second transparent and touch-sensitive input field; and
   a device that provides a haptically perceivable feedback to an operator only when the first input field and the second input field are simulataneously activated, wherein the second input field is disposed between the display and the first input field.

2. The operating unit as claimed in claim 1, wherein the first input field and the second input field comprises a resistance-controlled input field, or a capacitance-controlled input field, or a sound-wave controlled input field, or an optically-controlled input field.

3. The operating unit as claimed in claim 1, wherein the first input field and the second input field comprise different types of input fields.

4. The operating unit as claimed in claim 1, wherein the first input field covers a same area as the second input field and is arranged on the second input field.

5. The operating unit as claimed in claim 1, wherein the first input field and the second input field cover a same area as the display and are disposed on the display.

6. The operating unit as claimed in claim 1, wherein a front side of the display faces towards an operator, and wherein the first input field and the second input field partly cover the front side of the display.

7. The operating unit as claimed in claim 1, wherein the device is connected to a rear side of the display facing away from an operator or a carrier of the display.

8. The operating unit as claimed in claim 1, wherein the device comprises a vibration motor.

9. The operating unit as claimed in claim 1, wherein the display, the first input field and the second input field are connected to each other.

10. The operating unit as claimed in claim 1, wherein the haptically perceivable feedback comprises a vibration, a pulsing, or a shaking of at least an area of the operating unit.

11. A medical device, comprising:
   an operating unit comprising:
      a display;
      a first transparent and touch-sensitive input field;
      a second transparent and touch-sensitive input field; and
      a device that provides a haptically perceivable feedback to an operator only when the first input field and the second input field are simultaneously activated; and
   a positioning device that positions a component of the medical device, to a required position,
   wherein the second input field is disposed between the display and the first input field, and
   wherein the operating unit is configured to input the required position and correspondingly active the positioning device to position the component to the required position only when the first input field and the second input field are simultaneously activated.

12. The medical device as claimed in claim 11, further comprising a processing unit configured to:
   receive a first signal generated when the first input field is touched,
   receive a second signal generated when the second input field is actuated simultaneously, wherein the second input field is located in a direction of touch behind the first input field,
   process the first signal and the second signal only when the first signal and the second signal are presented simultaneously, and
   output a control signal after processing the first signal and the second signal for activating the device and the positioning device.

13. A method for performing a safety-relevant action by a medical device, comprising:
   touching a first input field of an operating unit of the medical device;
   simultaneously actuating a second input field of the operating unit, wherein the second input field is located in a direction of touch behind the first input field;
   positioning a component of the medical device a positioning device; and
   activating the positioning device to position the component to the required position only when the first input field and the second input field are simultaneously activated.

14. The method as claimed in claim 13, further comprising:
   generating a first signal when the first input field is touched;
   generating a second signal when the second input field is actuated simultaneously;
   transferring the first signal and the second signal to a processing unit of the medical device; and
   generating a control signal by the processing unit for performing a safety-relevant action only if the first signal and the second signal are presented simultaneously.

15. The method as claimed in claim 14, wherein duration of actuation of the operating unit is detected and the first signal and the second signal is accepted by the processing unit only if the duration exceeds a minimum duration.

\* \* \* \* \*